(12) United States Patent
Hubbard, Jr.

(10) Patent No.: US 6,360,597 B1
(45) Date of Patent: Mar. 26, 2002

(54) IN-SHOE REMOTE TELEMETRY GAIT ANALYSIS SYSTEM

(75) Inventor: James E. Hubbard, Jr., Derry, NH (US)

(73) Assignee: The Trustees of Boston University, Boston, MA (US)

(*) Notice: Subject to any disclaimer, the term of this patent is extended or adjusted under 35 U.S.C. 154(b) by 0 days.

(21) Appl. No.: 09/455,133

(22) Filed: Dec. 6, 1999

Related U.S. Application Data

(60) Continuation-in-part of application No. 09/169,759, filed on Oct. 9, 1998, which is a division of application No. 08/780,435, filed on Jan. 8, 1997, now Pat. No. 5,821,633.

(51) Int. Cl.$^7$ .................................................. A61B 5/00
(52) U.S. Cl. ...................................... 73/172; 73/862.46
(58) Field of Search ..................... 73/862.046, 862.041, 73/862.391, 172

(56) References Cited

U.S. PATENT DOCUMENTS

| | | | |
|---|---|---|---|
| 4,565,940 A | 1/1986 | Hubbard, Jr. ............... 310/326 |
| 4,626,730 A | 12/1986 | Hubbard, Jr. ............... 310/326 |
| 4,739,299 A | 4/1988 | Eventoff et al. .............. 338/99 |
| 4,810,992 A | 3/1989 | Eventoff ...................... 338/99 |
| 4,862,743 A | * 9/1989 | Seitz ........................... 73/172 |
| 4,876,758 A | * 10/1989 | Rolloff ........................ 12/142 |
| 4,935,614 A | 6/1990 | Hubbard, Jr. et al. .... 250/201.1 |
| 4,963,702 A | 10/1990 | Yaniger et al. ............... 178/18 |
| 5,026,977 A | 6/1991 | Hubbard, Jr. ............ 250/201.9 |
| 5,159,498 A | 10/1992 | Hubbard, Jr. ............... 359/847 |
| 5,209,126 A | 5/1993 | Grahn ................... 73/862.046 |
| 5,221,088 A | * 6/1993 | McTeigue et al. ....... 273/187.2 |
| 5,232,243 A | 8/1993 | Blackburn et al. .......... 280/732 |
| 5,237,542 A | 8/1993 | Burke et al. ................ 367/103 |
| 5,327,397 A | 7/1994 | Burke et al. ................ 367/103 |
| 5,400,662 A | 3/1995 | Tamori ................... 73/862.046 |
| 5,494,311 A | 2/1996 | Blackburn et al. .......... 280/735 |
| 5,503,029 A | 4/1996 | Tamori ................... 73/862.046 |
| 5,563,348 A | 10/1996 | Susuki et al. .................. 73/800 |
| 5,626,359 A | 5/1997 | Steffens, Jr. et al. ........ 280/735 |
| 5,653,462 A | 8/1997 | Breed et al. ................. 280/735 |
| 5,929,332 A | * 7/1999 | Brown ......................... 73/172 |

FOREIGN PATENT DOCUMENTS

| | | |
|---|---|---|
| DE | 3703630 | 8/1988 |
| DE | 3716168 | 11/1988 |
| DE | 4135784 | 5/1992 |
| DE | 19625730 A | 1/1998 |
| EP | 0222640 | 5/1987 |
| GB | 2197121 | 5/1988 |
| GB | 2252414 | 8/1992 |

\* cited by examiner

*Primary Examiner*—Max Noori
(74) *Attorney, Agent, or Firm*—Weingarten, Schurgin, Gagnebin & Lebovici LLP

(57) ABSTRACT

A gait analysis system includes a shoe insert for use in a shoe worn by a subject while walking as part of a process of collecting gait data. The insert has force-sensing sensors distributed to define a sensing aperture, and each sensor provides an electrical output signal. Processing apparatus is communicatively coupled with the sensors. The processing apparatus calculates a gait line represented by a series of points, wherein each point is calculated as a spatially-weighted average of samples of the sensor output signals over the sensing aperture. The processing apparatus includes a portable telemetry transmitter worn by the subject. The transmitter is connected to the sensors to receive the sensor output signals, and transmits a radio signal carrying the sensor information. A stationary receiver receives the sensor information in a transmission from the transmitter, and provides the sensor information to a personal computer or similar workstation.

6 Claims, 4 Drawing Sheets

IN-SHOE REMOTE TELEMETRY GAIT ANALYSIS SYSTEM

CROSS REFERENCE TO RELATED APPLICATIONS

This application is a continuation-in-part of U.S. patent application Ser. No. 09/169,759, filed Oct. 9, 1998, which is a division of U.S. patent application Ser. No. 08/780,435, filed Jan. 8, 1997, which issued on Oct. 13, 1998 as U.S. Pat. No. 5,821,633.

STATEMENT REGARDING FEDERALLY SPONSORED RESEARCH OR DEVELOPMENT

Not Applicable

BACKGROUND OF THE INVENTION

The present invention is related to the field of sensors and sensor systems used in analyzing the gait of a patient or other subject.

There has been a dramatic increase in the incidence of foot-related illnesses and other maladies that manifest themselves in a person's gait, and an attendant increase in the number of consultations with podiatrists and other medical professionals who deal with such medical problems. In an increasingly common scenario, a patient who visits a podiatrist is asked a series of questions about his problem, and an examination is performed, which typically includes observing the patient's gait during a brief walk. Oftentimes, after a possibly tentative diagnosis is reached, an orthotic device is prescribed. The patient returns for an additional office visit after the orthotic is made, and the orthotic is custom-fitted by the podiatrist. There may be one or more follow-up visits to determine whether the orthotic is achieving the desired results.

Current procedures like those described above can be excessively time-consuming, and tend to rely excessively on trial and error. Additionally, the patient feedback for prognosis purposes is very subjective. Thus, there has been a need for more objective techniques for gait analysis in the diagnosis, treatment and prognosis of podiatric illnesses.

Recently, gait analysis systems have been deployed that bring a desired measure of objectiveness to the diagnosis and treatment of podiatric illnesses. One such system utilizes a special shoe that is worn by a patient during an office visit. The footbed of the shoe contains a large number of small pressure sensors that generate electrical output signals indicative of pressure in a small area surrounding the sensor. These sensors are connected to a rather large data collection and analyzing system, using a lengthy cable harness with a number of wires carrying the sensor signals. The data analysis system is responsible for collecting data from the sensors at a given sampling rate while the patient takes a few steps, and then performs various signal processing on the large quantity of collected data in order to present diagnostically useful information to the physician using the system.

Gait analysis systems such as the one described above are considerably expensive, partly due to their use of numerous sensors and the attendant size of the data collection and signal processing tasks. In addition, because the patient is "tethered" to the system by the cable harness during use, such systems tend to be awkward to use, and are prone to cable-related malfunction. Moreover, the tethering can interfere with the analysis by artificially restricting the movement of the patient. Accordingly, there has been a need for improved gait analysis systems.

BRIEF SUMMARY OF THE INVENTION

In accordance with the present invention, a gait analysis system is disclosed that improves upon the above-mentioned drawbacks of present systems. The disclosed system includes a shoe insert configured for use in a shoe to be worn by a subject while walking as part of a process of collecting gait data. The shoe insert has a small number of force-sensing sensors distributed in a manner defining a sensing aperture. Each sensor provides an electrical output signal. Processing apparatus is communicatively coupled with the sensors on the shoe insert. The processing apparatus is operative to calculate a gait line that is represented by a series of points, wherein each point is calculated as a spatially-weighted average of samples of the sensor output signals over the sensing aperture.

In one embodiment, the processing apparatus includes a portable telemetry transmitter worn by the subject during the data collection process. The transmitter is connected to the sensors to receive the sensor output signals, and transmits a radio signal carrying the sensor information. A stationary receiver receives the sensor information in a transmission from the transmitter, and provides the sensor information to a personal computer or similar workstation. The use of a portable transmitter greatly enhances the usefulness of the system, by enabling the subject to walk in a normal manner unimpeded by electrical cables or other apparatus.

Other aspects, features, and advantages of the present invention are disclosed in the detailed description that follows.

DETAILED DESCRIPTION OF THE INVENTION

Figure 1:
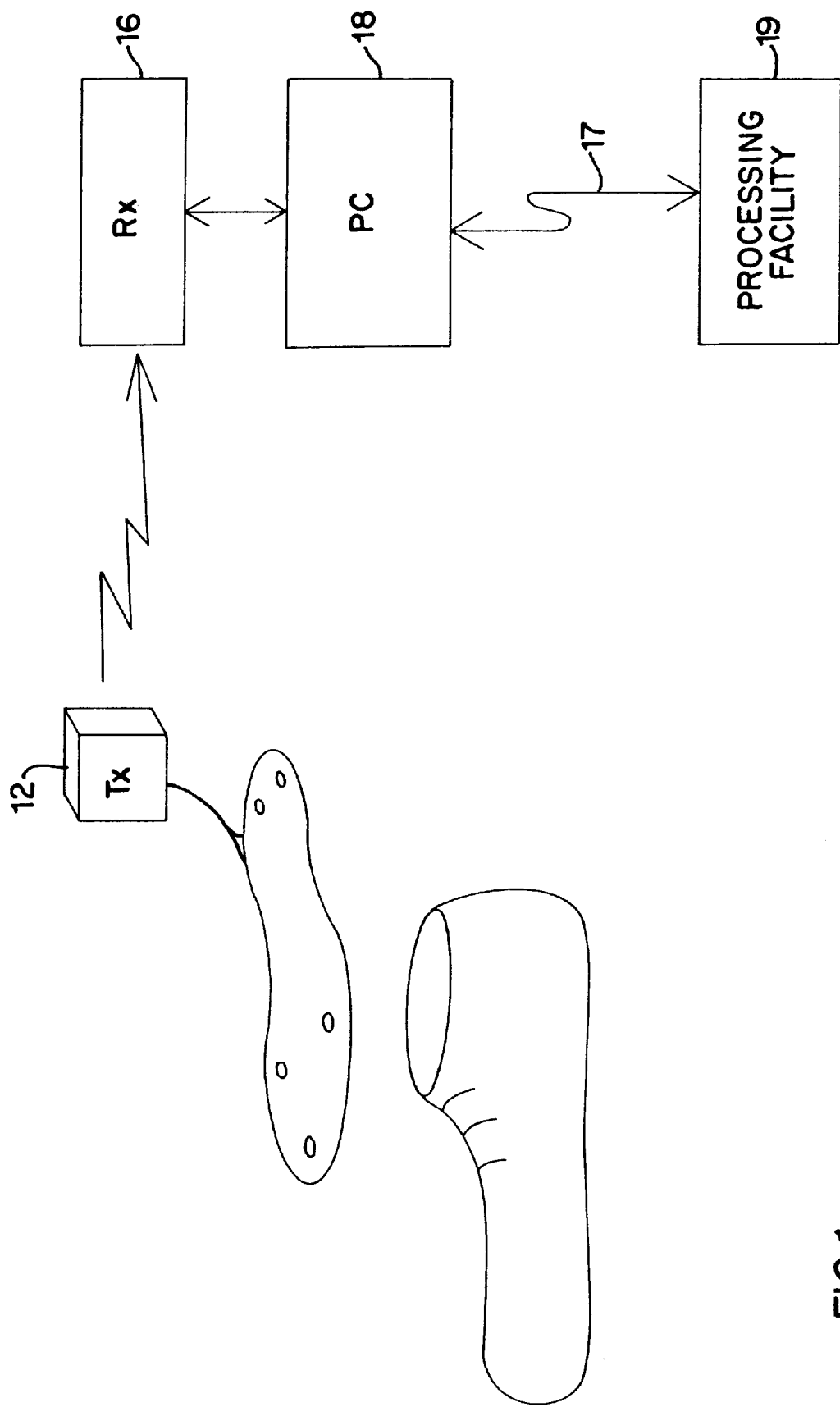
FIG. 1 is a block diagram of an in-shoe remote telemetry gait analysis system in accordance with the present invention.

In FIG. 1, a sensor-bearing shoe insert 10 is connected to a small, portable telemetry transmitter 12. As described in more detail below, the insert 10 has force sensors located in different positions. Each sensor is connected to a respective one of five input channels to the transmitter 12. The insert 10 is intended for use in a shoe 14 to be worn by a subject in order to collect gait data. A receiver 16 receives a radio signal emanating from the transmitter that carries sensor information signals representing the respective output values from the sensors. The sensor information recovered by the receiver 16 is provided to a personal computer (PC) 18 or similar workstation. Such a workstation may be located remotely over a link 17 at a central processing facility 19 with results sent back over the link 17.

During use of the gait analysis system of FIG. 1, a patient or other subject dons the shoe 14, attaches the transmitter 12 to his or her clothing (for example by clipping the transmitter 12 to a belt), and walks on a firm surface. The transmitter 12 receives output signals from the sensors indicative of the magnitude of force in areas of the insert 10 about the respective sensors, converts these signals into corresponding digital values, and transmits these digital values by appropriately modulating a radio frequency carrier. The receiver 16 receives the modulated carrier, performs appropriate de-modulation to recover the digital values, and forwards the digital values to the PC 18 using, for example, a serial communications link. An application program executing on the PC 18 makes various calculations on the sensor information, and presents the data to a user in graphical and other forms.

In one embodiment, the transmitter 12 and receiver 16 are components of a system called StrainLink™ available from MicroStrain, Inc. of Burlington, Vt., USA. The StrainLink system can accommodate up to 5 data channels in a so-called "pseudo differential mode" of operation. Each data input to the transmitter 12 is configured as a bridge in which one element is a force sensing resistor (FSR) used as a sensor in the insert 10. The transmitter applies respective programmable gains to the inputs from bridges before the conversion to digital form. Physically, the transmitter 12 in the StrainLink system occupies less than 1 cubic inch in volume.

Figure 2:
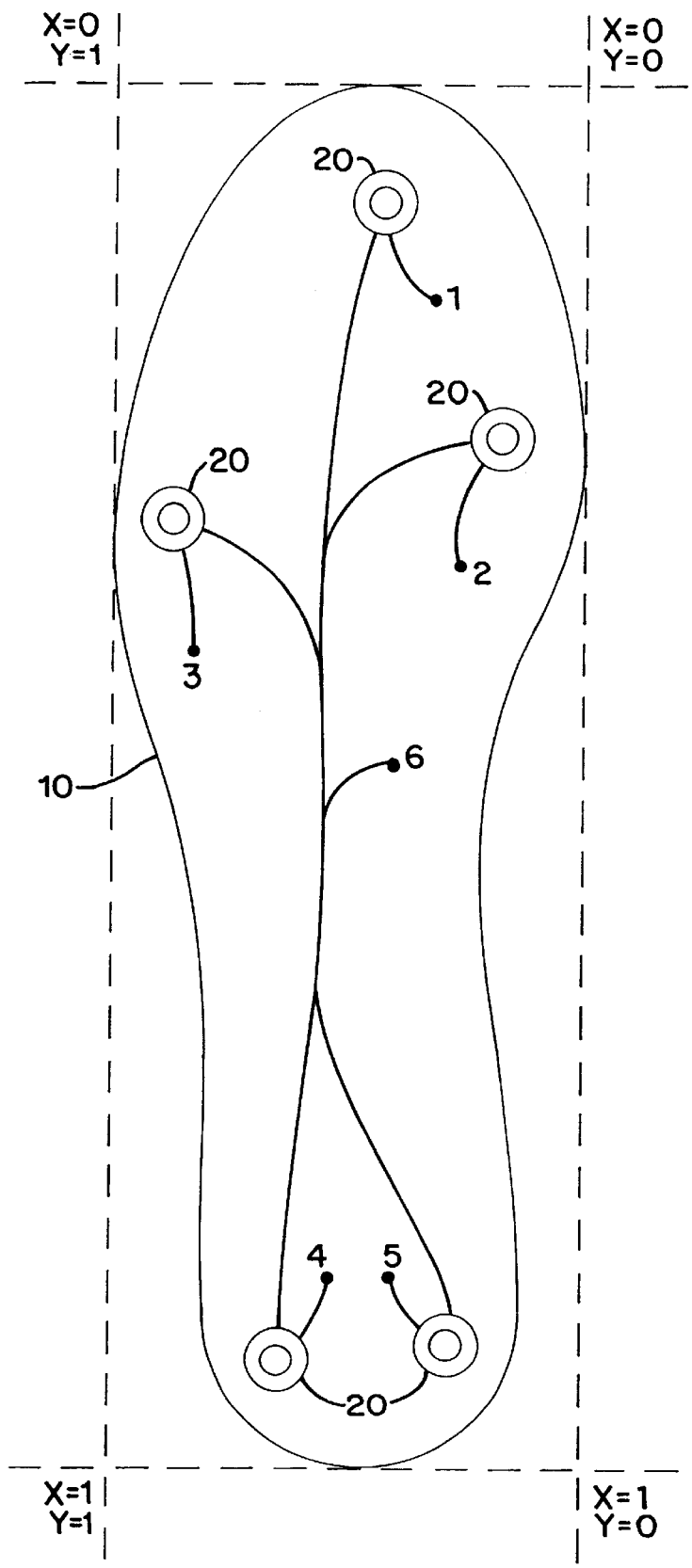
FIG. 2 is a plan diagram of a sensor-carrying shoe insert used in the gait analysis system of FIG. 1.

FIG. 2 shows the insert 10 in detail. The insert 10 consists primarily of a laminate body typically made of a polyester/foam core sandwich, although other materials and/or configurations are possible. As shown, five sensors 20 are disposed at key positions in the insert 10. In one embodiment, the sensors 20 are force sensing resistors or FSRs. Two electrical leads extend from each FSR 20. One lead from each FSR 20 is chosen as a ground lead, and the various ground leads are connected together as a common ground indicated as connection #6. The remaining leads are indicated as connections #1–#5. These leads are connected to the respective inputs of the transmitter 12 of FIG. 1 in a pseudo-differential bridge configuration, as discussed above. The resistance of each disk-shaped FSR 20 varies with the magnitude of the compressive force in the normal direction. When connected in a bridge circuit with a suitable current source, this varying resistance creates a correspondingly varying voltage signal. This voltage signal is amplified by an amplifier within the transmitter 12, and converted to a digital form for transmission to the receiver 16 as discussed above.

FIG. 2 also shows a coordinate system superimposed on the insert 10 that is used to identify locations. As shown, an "x" dimension extends longitudinally from the toe to the heel, and a "y" dimension extends laterally from the medial side (instep) to the lateral side (outstep). Based on the relative locations of the sensors 20 within this coordinate system, corresponding spatial weight values are used for certain calculations on the sensor data, as described below.

Figure 3:
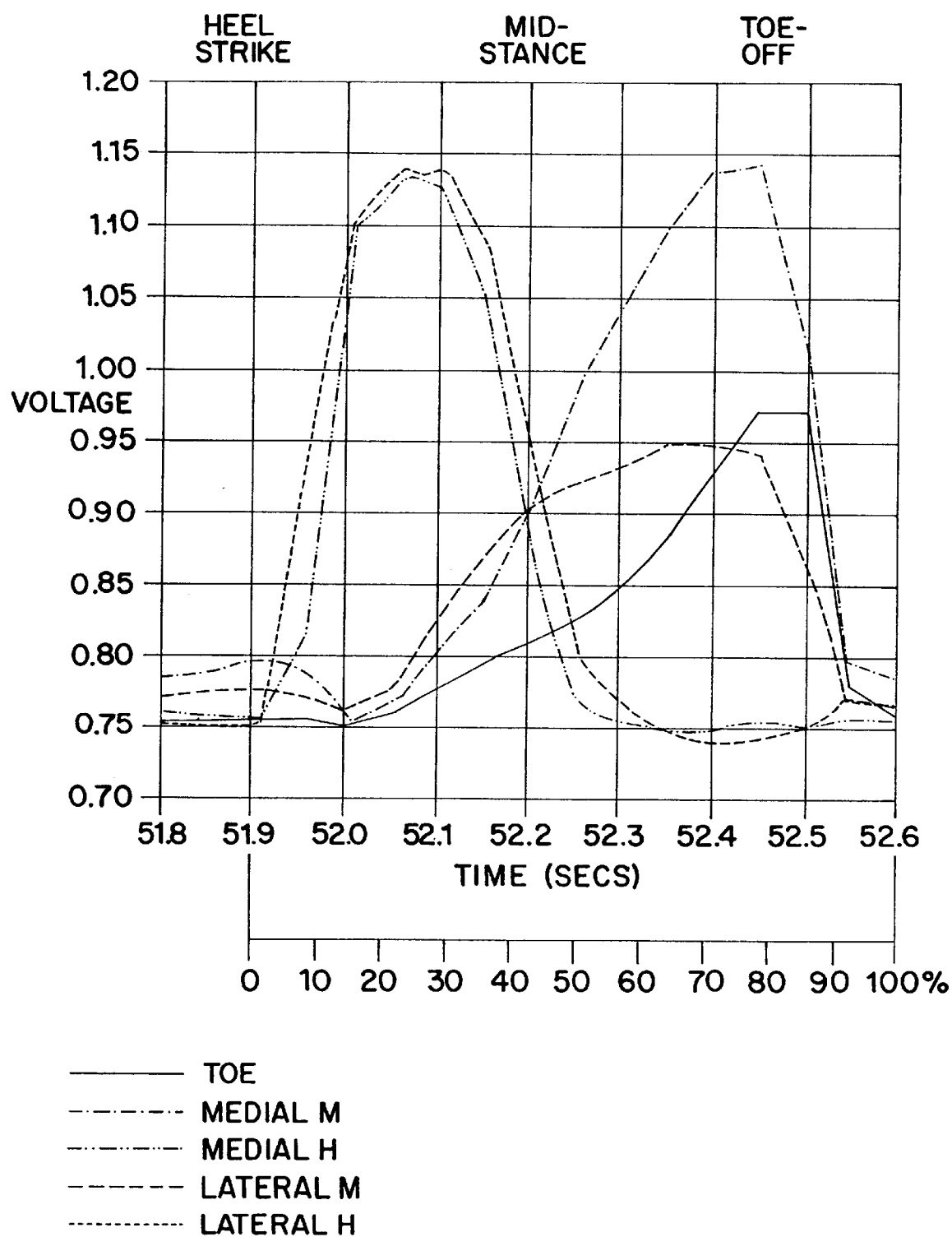
FIG. 3 is a plot of sensor output versus time in the system of FIG. 1 during the period when a subject's foot contacts a walking surface.
Figure 4:
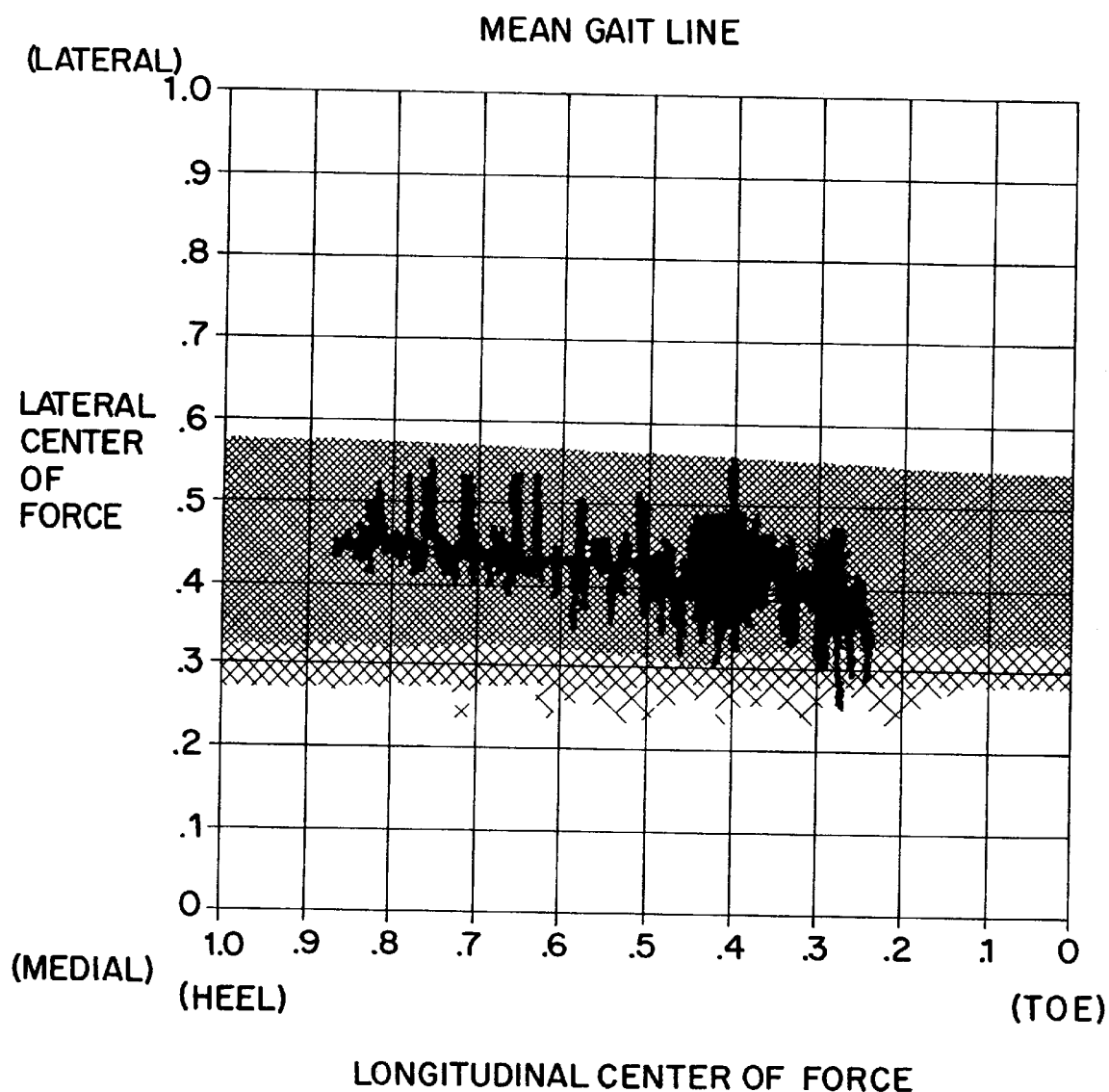
FIG. 4 is a plot of a mean gait line for a subject as derived from sensor data obtained in the system of FIG. 1.

The sensor data received by the PC 18 may be used in any of a variety of ways and for a variety of purposes. Gait analysis may require performing several different types of calculations on the data, comparing the data with historical values for the same subject, etc. FIG. 3 and FIG. 4, discussed below, illustrate two uses of the sensor data for gait analysis.

FIG. 3 shows a plot of sensor output as a function of time over the duration of the contact between a subject's foot and a walking surface. The time dimension is given as both absolute values (51.8 seconds through 52.6 seconds) and as a percent of the entire contact phase. The vertical dimension is pressure, reported as a voltage. During analysis, the pressure values are normalized by the patient's weight. The plot illustrates the following three phases of contact: (1) heel strike, indicated by relative maxima for the sensors located at the heel; (2) toe-off, indicated by maxima for the sensors located at the metatarsals and hallux; and (3) mid-stance, which is the interval between heel strike and toe-off. Additionally, the following points of diagnostic interest are indicated:

1. Heel lift-off at about 55% through the contact phase. Normal range is 50–65%

2. Forefoot contact at about 15%. Normal range is 16–23%.

3. Forefoot peak pressure at about 75%. Normal range is 70–80%.

Additionally, in the plot of FIG. 3 the peak for the medial metatarsal is substantially greater than the peak for the lateral metatarsal, which is symptomatic of over-pronation. Thus it will be appreciated that a good deal of diagnostically useful information can be obtained from the sensor output signals in the gait analysis system of FIG. 1.

FIG. 4 shows a plot of a so-called "gait line", which represents the movement of the center of force throughout the contact phase of a step. The points that constitute the gait line are each calculated from samples of the sensor signals. These points are calculated using spatial weighting techniques like those described in the above-referenced parent patent and application, incorporated herein by reference. In particular, the spatial weighting for each sensor is directly related to its relative location on the insert 10 as shown in FIG. 2. Thus, in the illustrated embodiment, the weights are assigned as follows:

| Sensor | $w_x$ | $w_y$ |
|---|---|---|
| 1 | .078 | .440 |
| 2 | .253 | .174 |
| 3 | .281 | .860 |
| 4 | .924 | .727 |
| 5 | .924 | .340 |

Each point in the gait line is then calculated as a weighted average of the samples of the sensor output signals. More formally, if the point on the gait line is represented as ($GL_x$, $GL_y$) and the scalar output of the ith sensor is $S_i$, then:

$GL_x = \Sigma(S_i \cdot W_{xi})$ for all i; and $GL_y = \Sigma(S_i \cdot W_{yi})$ for all i.

The above represents the calculation of a first-order moment of the sensor data using uniform spatial weighting. It will be appreciated that in alternative embodiments the calculation of higher-order moments may be useful. Also, it is possible to employ non-uniform weighting, and to employ more or fewer sensors to achieve different tradeoffs between resolution and complexity/cost.

An in-shoe remote telemetry gait analysis system has been described. It will be apparent to those skilled in the art that other modifications to and variations of the above-described technique are possible without departing from the inventive concepts disclosed herein. Accordingly, the invention should be viewed as limited solely by the scope and spirit of the appended claims.

What is claimed is:

1. A method for gait analysis, comprising:

fitting a shoe insert in a shoe, the shoe insert having force-sensing sensors disposed at predetermined locations, each sensor providing a respective electrical output signal;

having a subject wear the shoe with insert while walking;

obtaining samples of the electrical output signals of the sensors during the subject's walking; and from the samples of the sensor output signals, calculating a gait line being represented by a series of points in a two-dimensional space corresponding to a sensing aperture extending across the shoe insert, each point being calculated as a spatially-weighted average of respective samples of the sensor information signals so as to indicate at least a first-order moment of the forces applied to the shoe insert by the subject during the gait analysis process.

2. A method according to claim 1, further comprising having the subject wear a portable telemetry unit connected to the sensors during the gait analysis process, and wherein obtaining samples of the electrical output signals of the sensors comprises:

generating a radio signal at the telemetry unit, the radio signal carrying sensor information signals, each sensor information signal being obtained from a corresponding one of the sensor output signals; and receiving the radio signal from the telemetry unit and generating digital data representative of the sensor output signals, the digital data being used in the calculation of the gait line.

3. A method according to claim 1, further comprising determining, from the sensor output signals, respective times at which heel strike and toe-off occur during a phase in which the subject's foot is in contact with a walking surface, and comparing these times with pre-determined normal ranges for heel strike and toe-off.

4. A method according to claim 1, further. comprising determining an extent of pronation from the sensor output signals.

5. A method according to claim 1, further comprising determining an extent of supination from the sensor output signals.

6. A method according to claim 1, further comprising including an orthotic in the shoe during the gait analysis process.

* * * * *